United States Patent
Jang et al.

(10) Patent No.: US 8,699,661 B2
(45) Date of Patent: Apr. 15, 2014

(54) APPARATUS AND METHOD FOR IMAGING BREAST

(75) Inventors: Kwang Eun Jang, Busan-si (KR); Jong Ha Lee, Hwaseong-si (KR); Young Hun Sung, Hwaseong-si (KR); Sung Su Kim, Yongin-si (KR); Hyun Hwa Oh, Hwseong-si (KR); Seok Min Han, Seongnam-si (KR); Dong Goo Kang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 353 days.

(21) Appl. No.: 13/169,084

(22) Filed: Jun. 27, 2011

(65) Prior Publication Data
US 2012/0057672 A1    Mar. 8, 2012

(30) Foreign Application Priority Data
Sep. 7, 2010   (KR) ................ 10-2010-0087488

(51) Int. Cl.
*A61B 6/04* (2006.01)
(52) U.S. Cl.
USPC ............................................. 378/37; 378/62
(58) Field of Classification Search
USPC ........................ 378/37, 62, 97, 108
See application file for complete search history.

(56) References Cited

U.S. PATENT DOCUMENTS

| | | | |
|---|---|---|---|
| 7,062,006 B1 | 6/2006 | Pelc et al. | |
| 7,330,529 B2 | 2/2008 | Kautzer et al. | |
| 7,356,113 B2 | 4/2008 | Wu et al. | |
| 7,466,795 B2 | 12/2008 | Eberhard et al. | |
| 7,558,366 B2 | 7/2009 | Barth et al. | |
| 2008/0123803 A1* | 5/2008 | De Man et al. | 378/9 |
| 2009/0022264 A1* | 1/2009 | Zhou et al. | 378/5 |

FOREIGN PATENT DOCUMENTS

JP   2008-284081   11/2008

\* cited by examiner

*Primary Examiner* — Hoon Song
(74) *Attorney, Agent, or Firm* — NSIP Law

(57) ABSTRACT

An apparatus and method for imaging a breast is provided. The apparatus for imaging a breast includes a first X-ray emission unit configured to emit an X-ray of a first dose to a breast, a second X-ray emission unit configured to emit one or more X-rays of a second dose to the breast, the first dose being greater than the second dose, an X-ray detection unit configured to detect the X-ray of the first dose or the one or more X-rays of the second dose to thereby generate one or more image frames regarding the breast, and an image generation unit configured to generate image data regarding the breast based on the generated one or more image frames.

18 Claims, 4 Drawing Sheets

100

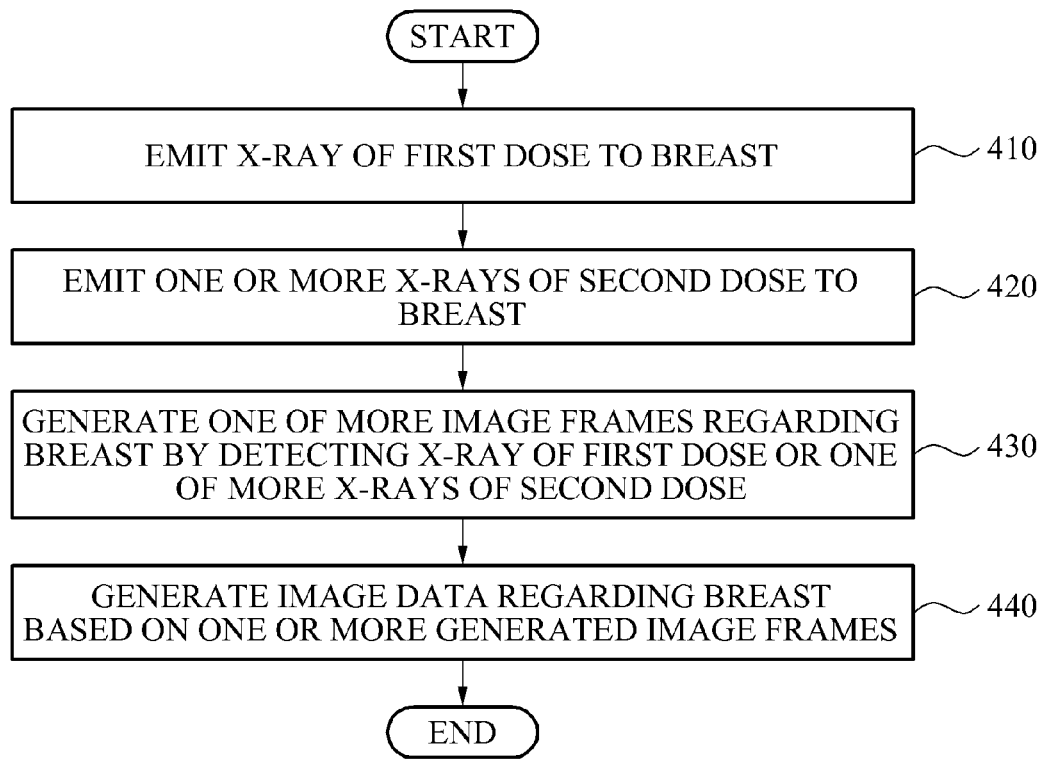

APPARATUS AND METHOD FOR IMAGING BREAST

CROSS-REFERENCE TO RELATED APPLICATION

This application claims the benefit under 35 U.S.C. §119 (a) of Korean Patent Application No. 10-2010-0087488, filed on Sep. 7, 2010, in the Korean Intellectual Property Office, the entire disclosure of which is incorporated herein by reference for all purposes.

BACKGROUND

1. Field

The following description relates to an apparatus and method for imaging a breast, and more particularly, to an apparatus and method for imaging a breast more quickly and accurately by emitting a plurality of X-rays of different doses to the breast that is an object of examination.

2. Description of Related Art

Currently, X-ray mammography is the most widely used breast imaging technology. Recently, full field digital mammography (FFDM), that is, a digital mammography system using a flat panel detector, has become widely used. FFDM is highly economical due to the use of low-cost equipment. In addition, FFDM has an imaging operation that is relatively fast and convenient to use.

X-ray mammography is very suitable for detecting micro calcification (MC) in a breast. However, X-ray mammography is relatively poor at detection when a main lesion is a mass. In addition, X-ray mammography has a reduced diagnostic accuracy in the examination of a dense breast.

Unlike conventional 2-dimensional X-ray examination methods, a tomosynthesis scheme images a breast at a plurality of different angles (e.g., about seven to thirty different angles), thereby overcoming limits caused by tissue overlap. Therefore, the tomosynthesis scheme is expected to replace conventional X-ray mammography in the future.

However, since the tomosynthesis scheme is slow in operation, a patient may move or be moving due to breathing and heartbeats during the long time that is required by the tomosynthesis scheme to produce an image. In addition, the tomosynthesis machine is susceptible to movement of its own during the imaging time. Such movements by the examination subject or the tomosynthesis machine may produce images that are not optimal or, in some cases, incomprehensible.

Accordingly, there is a demand for a solution to the slow acquisition of information that is provided by conventional breast imaging technology.

SUMMARY

In one general aspect, there is provided an apparatus for imaging a breast, including a first X-ray emission unit configured to emit an X-ray of a first dose to a breast, a second X-ray emission unit configured to emit one or more X-rays of a second dose to the breast, the first dose being greater than the second dose, an X-ray detection unit configured to detect the X-ray of the first dose or the one or more X-rays of the second dose to thereby generate one or more image frames regarding the breast, and an image generation unit configured to generate image data regarding the breast based on the generated one or more image frames.

The apparatus may further provide that the first X-ray emission unit is further configured to emit an X-ray of a third dose to generate pilot image data, the X-ray detection unit is further configured to detect the X-ray of the third dose to generate one or more pilot image frames regarding the breast, and the image generation unit is further configured to generate the pilot image data based on the one or more pilot image frames.

The apparatus may further provide that the third dose is less than the first dose.

The apparatus may further include a parameter adjustment unit configured to adjust a parameter regarding a dose of an X-ray generated from the first X-ray emission unit or the second X-ray emission unit, based on the pilot image data.

The apparatus may further provide that the first X-ray emission unit is further configured to emit the X-ray of the first dose based on the adjusted parameter, and the second X-ray emission unit is further configured to emit the one or more X-rays of the second dose based on the adjusted parameter.

The apparatus may further provide that the image generation unit is further configured to generate the image data by equalizing the one or more image frames.

The apparatus may further provide that the first X-ray emission unit or the second X-ray emission unit is further configured to emit an X-ray of one or more energy spectrums from a plurality of regions of the breast.

The apparatus may further provide that the X-ray detection unit is further configured to detect the X-ray of the one or more energy spectrums emitted from the plurality of regions of the breast to generate a plurality of image groups including the one or more image frames.

The apparatus may further provide that the image generation unit is further configured to compose the one or more image frames constituting the plurality of image groups to generate the image data.

The apparatus may further provide that the image generation unit is further configured to combine and equalize the one or more image frames constituting the plurality of image groups to generate three-dimensional image data regarding the breast.

The apparatus may further provide that the first X-ray emission unit is fixedly disposed in a center of an X-ray source array, the X-ray source array including the first X-ray emission unit and a plurality of second X-ray emission units, the plurality of second X-ray emission units including the second X-ray emission unit, and each of the second X-ray emission units is fixedly disposed in different positions of the X-ray source array.

The apparatus may further include a first X-ray source array, a second X-ray source array, and a third X-ray source array, the second and third X-ray source arrays being disposed on opposite sides of the first X-ray source array. The first X-ray emission unit is disposed in the first X-ray source array, and a plurality of second X-ray emission units is disposed in the second X-ray source array or the third X-ray source array, the plurality of second X-ray emission units including the second X-ray emission unit.

The apparatus may further provide that the first X-ray emission unit is an X-ray source array including one or more X-ray source according to a thermionic emission type, and the second X-ray emission unit is an X-ray source array including one or more X-ray source according to a field emission type.

The apparatus may further provide that a cathode of the field emission type X-ray source comprises a carbon nanotube (CNT), a metallic filament tube, or any combination thereof.

In another general aspect, there is provided a method of imaging a breast, including emitting an X-ray of a first dose to a breast, emitting an X-ray of a second dose to the breast, the first dose being greater than the second dose, generating one or more image frames regarding the breast, the generating of the one or more image frames including detecting the X-ray of the first dose or the X-ray of the second dose that have passed through the breast, and generating image data regarding the breast based on the generating of the one or more image frames.

The method may further include emitting an X-ray of a third dose to generate pilot image data, generating one or more pilot image frames regarding the breast, the generating of the one or more pilot image frames including detecting the X-ray of the third dose, and generating the pilot image data based on the generating of the one or more pilot image frames.

The method may further provide that the third dose is less than the first dose.

The method may further include adjusting a parameter regarding the X-ray of the first dose or the X-ray of the second dose, based on the pilot image data.

The method may further include emitting the X-ray of the first dose based on the adjusted parameter, and emitting the X-ray of the second dose based on the adjusted parameter.

In another general aspect, there is provided a non-transitory computer readable recording medium storing a program to cause a computer to implement the method of the above-referenced general aspect.

Other features and aspects may be apparent from the following detailed description, the drawings, and the claims.

BRIEF DESCRIPTION OF THE DRAWINGS

FIG. 4 is a flowchart illustrating an example of a method of imaging a breast.

Figure 1:
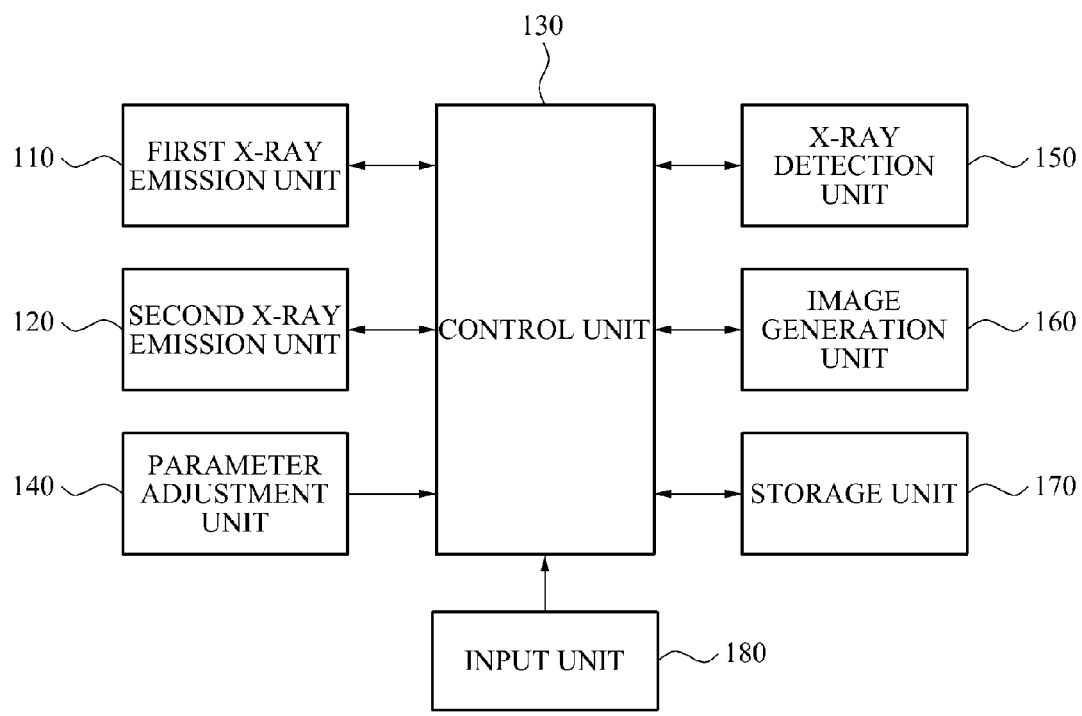
FIG. 1 is a block diagram illustrating an example of a configuration of a breast imaging apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods and apparatuses described herein. Accordingly, various changes, modifications, and equivalents of the apparatuses and/or methods described herein will be suggested to those of ordinary skill in the art. In addition, descriptions of well-known functions and constructions may be omitted for increased clarity and conciseness.

FIG. 1 is a block diagram illustrating an example of a configuration of a breast imaging apparatus 100.

Referring to FIG. 1, the breast imaging apparatus 100 may include a first X-ray emission unit 110, a second X-ray emission unit 120, a control unit 130, an X-ray detection unit 150, and an image generation unit 160.

According to one general aspect, the breast imaging apparatus 100 may further include a parameter adjustment unit 140 and a storage unit 170. In addition, an input unit 180 may be additionally provided to enable a user to input data and control the parameter adjustment unit 140 and the storage unit 170 through the control unit 130.

The input unit 180 may receive various types of data for operation of the breast imaging apparatus 100, the data provided by a user such as a doctor or an operator through input parts (not shown) provided outside of the breast imaging apparatus 100.

Therefore, in the breast imaging apparatus 100, when the user operates the input parts to start breast imaging, the input unit 180 is input with a breast-imaging signal.

The first X-ray emission unit 110 of the breast imaging apparatus 100 emits an X-ray of a first dose onto a breast that is an object of examination. One or more second X-ray emission units 120 emit one or more X-rays of a second dose onto the breast.

A single X-ray source array may include the first X-ray emission unit 110 and the one or more second X-ray emission units 120. Here, the X-ray source array refers to a structure having a plurality of devices that are connected and configured to generate X-rays, such as the first X-ray emission unit 110 and the one or more second X-ray emission units 120.

The first X-ray emission unit 110 may be fixedly disposed in a center of the X-ray source array. Each of the one or more second X-ray emission units 120 may be fixedly disposed in positions of the X-ray source array that are different from the first X-ray emission unit 110.

Alternatively, the breast imaging apparatus 100 may include a plurality of X-ray source arrays. For example, the plurality of X-ray source arrays may include the first X-ray source array, a second X-ray source array, and a third X-ray source array, the second and third X-ray source arrays being respectively disposed on either side of the first X-ray source array.

The first X-ray emission unit 110 may be disposed in the first X-ray source array while the one or more second X-ray emission units 120 may be disposed in the second X-ray source array, the third X-ray source array, or any combination thereof.

The X-ray source arrays may be arranged in various manners, such as a linear type, an arc type, and the like. Intervals between the X-ray emission units may be uniform or non-uniform.

In other words, in an example, one or more of the X-ray source arrays may refer to a plurality of emission units focusing on the breast.

The first X-ray emission unit 110 may be in the form of an X-ray source array including one or more X-ray sources of a thermionic emission type. The one or more second X-ray emission units 120 may be in the form of an X-ray source array including one or more X-ray sources of a field emission type.

A cathode of the one or more field emission type X-ray sources may include various types of X-ray generating tips, such as a carbon nanotube (CNT) or a metallic filament tube.

The control unit 130 may receive control signals related to the respective components of the breast imaging apparatus 100 and, according to the received control signals, control the respective components according to the user's operation intentions.

Doses of the X-ray emitted from the first X-ray emission unit 110 and the one or more X-rays emitted respectively from the one or more second X-ray emission units 120 may be uniform or non-uniform.

For example, in the breast imaging apparatus 100, the breast may be imaged more finely and accurately by varying the doses of the X-rays emitted from the first X-ray emission unit 110 and the one or more second X-ray emission units 120.

According to the breast imaging apparatus 100, the breast may be imaged by emitting the X-rays at various angles. When a high dose is applied to a clinically significant region, the radiation may be efficiently used while ultimately reducing the radiation dose.

For example, a fine image may be obtained by emitting an X-ray of a high dose to a region where an angle between the breast and the respective X-ray emission unit is 0°. In addition, radiation use efficiency may be maximized by emitting an X-ray of a low dose to a region where the breast and the respective X-ray emission unit form a predetermined angle.

That is, when the X-ray of the first dose is emitted to a center of the breast, which is a region where the first X-ray emission unit 110 and the breast forms an angle of 0°, while the one or more X-rays of the second dose are emitted at different angles to the breast, the first dose is greater than the second dose. Accordingly, radiation use efficiency may be maximized.

The X-ray detection unit 150 may generate one or more image frames regarding the breast by detecting the X-ray of the first dose or the one or more X-rays of the second dose that have passed through the breast.

The image generation unit 160 may generate image data regarding the breast based on the one or more image frames. For generation of image data, the image generation unit 160 may equalize the one or more image frames.

Moreover, the one or more image frames may have different resolution and noise characteristics due to different respective doses. Therefore, equalization is performed with respect to the one or more image frames constituting the image data to make the resolution and noise characteristics more uniform.

Hereinafter, an example of a process of generating the image data of the breast imaging apparatus 100 will be described.

According to one example, the first X-ray emission unit 110 emits an X-ray of a third dose to generate pilot image data. The X-ray detection unit 150 detects the X-ray of the third dose, and thereby generates one or more pilot image frames regarding the breast. The image generation unit 160 generates the pilot image data based on the one or more pilot image frames.

According to the breast imaging apparatus 100, the pilot image data is generated based on the pilot image frame before final image data is generated. Next, to adjust the doses of the X-rays, the pilot image data is analyzed or inspected. Consequently, more accurate image data may be obtained.

For example, in the breast imaging apparatus 100, the third dose may be less than the first dose to generate the one or more pilot image frames and the pilot image data.

The parameter adjustment unit 140 may adjust a parameter regarding a dose of the X-ray generated from the first X-ray emission unit 110 and doses of the one or more X-rays generated from the one or more second X-ray emission units 120 based on the pilot image data.

The first X-ray emission unit 110 may emit the X-ray of the first dose based on the adjusted parameter. The one or more second X-ray emission units 120 may emit the one or more X-rays of the second dose based on the adjusted parameter.

The X-ray detection unit 150 may detect either the emitted X-ray of the first dose based on the adjusted parameter or the emitted one or more X-rays of the second dose based on the adjusted parameter, thereby generating one or more final image frames regarding the breast.

The image generation unit 160 may generate final image data regarding the breast based on the one or more final image frames. Here, the final image data may be generated through equalization of the one or more final image frames.

Thus, the breast imaging apparatus 100 may more accurately image micro calcification (MC) and masses present in the breast by emitting X-rays of different energy spectrums from different regions above the breast that is the examination object.

The first X-ray emission unit 110 or the one or more second X-ray emission units 120 may emit an X-ray having one or more energy spectrums from a plurality of regions above the breast.

For convenience of description, hereinafter, it will be presumed that the X-ray having the one or more energy spectrums is emitted from any one of the first X-ray emission unit 110 and the one or more second X-ray emission units 120 in a plurality of regions above the breast. However, it is not limited thereto, and the X-ray having the one or more energy spectrums may be emitted from a plurality of X-ray emission units in an additional plurality of regions above the breast.

For example, an X-ray emission unit may emit X-rays having two different energy spectrums from a first region of the breast that is the examination object. Moreover, the one or more second X-ray emission units 120 may emit an X-ray of a first energy spectrum and an X-ray of a second energy spectrum from the first region. The first region may be the center of the breast.

After emission of the X-ray to the breast from the first region, the X-ray emission unit may emit an X-ray having a third energy spectrum to the breast from a second region different from the first region. The third energy spectrum may be different from or the same as the first and second energy spectrums.

The X-ray detection unit 150 may generate a plurality of image groups including a plurality of the image frames by detecting the X-ray having the one or more energy spectrums emitted from the plurality of regions.

For example, the X-ray detection unit 150 may generate the plurality of image frames regarding the breast by detecting the X-ray emitted from the X-ray emission unit that has passed through the breast. The X-ray detection unit 150 may include a charge-coupled device (CCD).

The X-ray detection unit 150 may generate the plurality of image frames by detecting the X-ray emitted from the first region above the breast, accordingly generating a first image group including the plurality of image frames.

The X-ray detection unit 150 may generate the plurality of image frames by detecting the X-ray having the third energy spectrum emitted from the second region of the breast, accordingly generating a second image group including the plurality of image frames.

The image generation unit 160 may generate the image data by combining the plurality of image frames constituting the plurality of image groups.

The image generation unit 160 may generate three-dimensional (3D) image data regarding the breast by combining the plurality of image frames constituting the first image group and the second image group generated by the X-ray detection unit 150. During the generation of the 3D image data, the image generation unit 160 may equalize the image frames constituting the 3D image data.

Upon input of the breast imaging signal to the input unit 180, the control unit 130 may control the first X-ray emission unit 110, the one or more second X-ray emission units 120, the X-ray detection unit 150, and the image generation unit 160 to generate the image data regarding the breast. In addition, the control unit 130 stores the generated image data in the storage unit 170.

The breast imaging apparatus 100 may transmit the image data to a display apparatus electrically connected thereto or may include a display unit (not shown) to display the image data.

Figure 2:
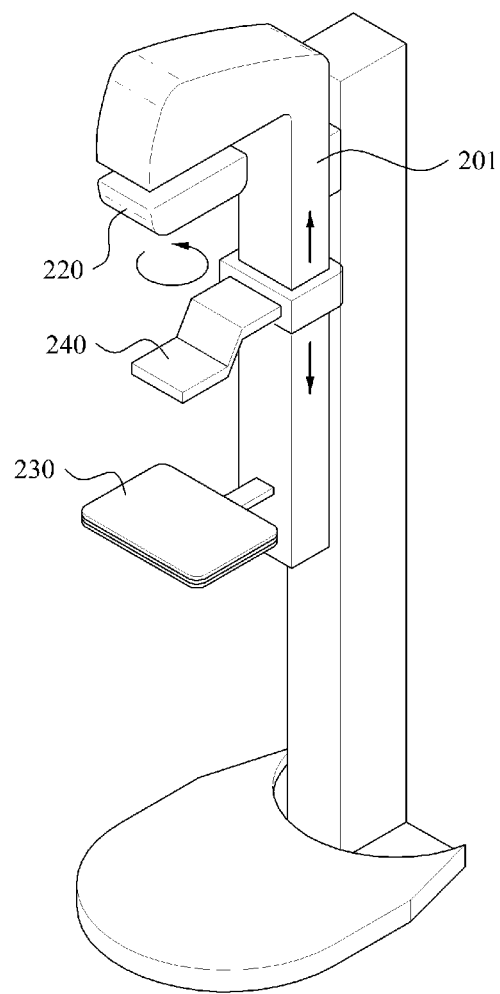
FIG. 2 is a diagram illustrating an example of an external structure of a breast imaging apparatus.

FIG. 2 is a view showing an example of an external structure of a breast imaging apparatus 200.

Referring to FIG. 2, the breast imaging apparatus 200 includes an X-ray source array 220 including the first X-ray emission unit 110 and the one or more second X-ray emission units 120, an X-ray detection unit 230, and a compression plate 240.

According to the example of the breast imaging apparatus 200 shown in FIG. 2, a patient's breast may be imaged in a standing position with the breast compressed between the compression plate 240 and the X-ray detection unit 230. Here, the external structure of the breast imaging apparatus 200 is not limited to the example shown in FIG. 2. That is, the breast imaging apparatus 200 may be configured to allow the patient to undergo the breast imaging in a sitting position or standing position.

In the case where the patient is standing, the breast may be compressed by the compression plate 240 and the X-ray detection unit 230 in an up and down direction, a lateral direction, or a forward and backward direction. A main body 201 of the breast imaging apparatus 200 may be rotated to image the breast in the lateral direction or the forward and backward direction.

In the state where the breast is compressed between the compression plate 240 and the X-ray detection unit 230, a doctor or an operator operates the breast imaging apparatus 200 to start the imaging. Upon starting the imaging operation, the X-ray source array 220 emits the X-ray of the first dose and the one or more X-rays of the second dose to the breast.

Figure 3:
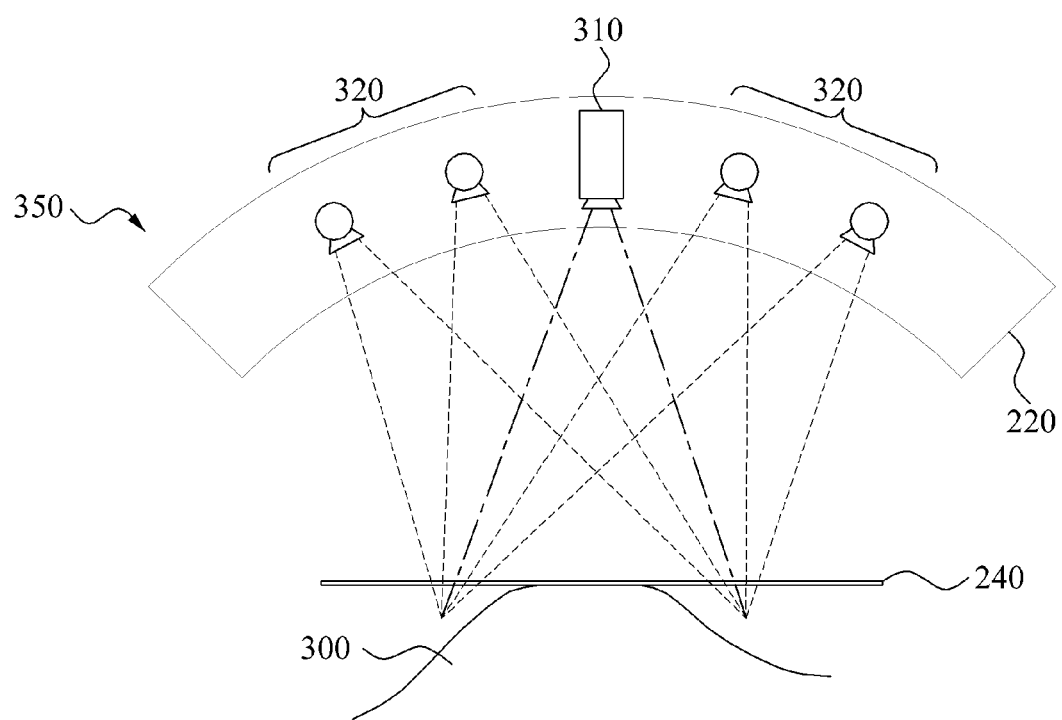
FIG. 3 is a diagram illustrating an example of an operational state of a breast imaging apparatus.

FIG. 3 is a diagram illustrating an example of an operational state of a breast imaging apparatus 350.

Referring to FIG. 3, a first X-ray emission unit 310 and a plurality of second X-ray emission units 320 arranged in the X-ray source array 220 may emit X-rays of the same dose or different doses toward a breast 300 compressed by the compression plate 240.

As described above, the X-ray source array 220 may be configured by connecting a plurality of devices for generating an X-ray, such as the first X-ray emission unit 310 and the plurality of second X-ray emission units 320. FIG. 3 shows an example where a single first X-ray emission unit 310 is disposed in a center of the X-ray source array 220 and the plurality of the second X-ray emission units 320 are arranged in respectively different positions of the X-ray source array 220. The respectively different positions of the plurality of second X-ray emission units 320 may be on opposite sides of the first X-ray emission unit 310.

For another example, the breast imaging apparatus 350 may include a plurality of X-ray source arrays, for example, a first X-ray source array, a second X-ray source array, and a third X-ray source array. The second and third X-ray source arrays may be disposed on opposite sides of the first X-ray source array.

The first X-ray emission unit 310 may be disposed in the first X-ray source array whereas the plurality of second X-ray emission units 320 may be disposed in the second and the third X-ray source arrays.

In addition, as shown in FIG. 3, the X-ray source array 220 may have an arc shape. A plurality of the X-ray emission units may be arranged at uniform intervals along the arc while focusing on the breast.

The X-ray of the first dose emitted from the first X-ray emission unit 310 and the one or more X-rays of the second dose emitted from the plurality of second X-ray emission units 320 may be uniform or non-uniform.

For example, the breast imaging apparatus 350 may be capable of imaging the breast more finely and accurately by emitting different doses of the X-rays from the first X-ray emission unit 310 and the plurality of second X-ray emission units 320.

The breast imaging apparatus 350 may emit the X-rays at various angles, and, for example, may apply a high dose of radiation to the clinically significant region. Accordingly, radiation use efficiency is maximized while reducing the radiation dose.

For example, the X-ray of a high dose is emitted by the first X-ray emission unit 310 to the center of the breast, where an angle formed by the breast and the X-ray emission unit is 0°, thereby generating a fine image. In addition, the X-ray of a low dose is emitted by the plurality of second X-ray emission units 320 to regions where the breast and the X-ray emission unit form a predetermined angle, thereby maximizing radiation use efficiency.

That is, according to the embodiment, the X-ray of the first dose is emitted to the center of the breast, where the angle formed by the first X-ray emission unit 110 and the breast is 0°, and the one or more X-rays of the second dose are emitted to the breast at different angles. Here, since the first dose is greater than the second dose, radiation use efficiency may be maximized.

For example, a region where the breast and the X-ray emission unit form approximately 0°, that is, the center of the breast in the drawing, may greatly influence an X-Y plane. An image taken from a lateral side may become information in a depth direction, that is, Z-direction information.

Although the Z-direction information is used to overcome limits in case of a dense breast, resolution of the X-Y plane is more significant than accuracy in the depth direction in diagnosing the breast.

Therefore, the breast imaging apparatus 350 may maximize the radiation use efficiency by emitting the high dose X-ray by the first X-ray emission unit 310 to the X-Y plane and emitting the low dose X-ray by the plurality of second X-ray emission units 320 in the Z-direction.

FIG. 4 is a flowchart illustrating an example of a method of imaging a breast.

The breast imaging apparatuses 100, 200, 350 emits the X-ray of the first dose onto the breast in operation 410, and emits the one or more X-rays of the second dose onto the breast in operation 420.

Here, the first dose may be greater than the second dose.

The breast imaging apparatuses 100, 200, 350 may generate one or more image frames regarding the breast by detecting the X-ray of the first dose or the one or more X-rays of the second dose passed through the breast, in operation 430.

The breast imaging apparatuses 100, 200, 350 may generate the image data regarding the breast based on one or more generated image frames in operation 440.

The above-described embodiments may be recorded, stored, or fixed in one or more non-transitory computer-readable media that includes program instructions to be implemented by a computer to cause a processor to execute or perform the program instructions. The media may also include, alone or in combination with the program instructions, data files, data structures, and the like. The program instructions recorded on the media may be those specially designed and constructed, or they may be of the kind well known and available to those having skill in the computer software arts. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher-level code that may be executed by the computer using an interpreter. The described hardware devices may be configured to act as one or more software modules in order to perform the operations and methods described above, or vice versa.

According to the examples described above, information regarding a breast may be acquired more quickly and accurately by emitting X-rays of different doses to the breast.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for imaging a breast, comprising:
a first X-ray emission unit configured to emit an X-ray of a first dose and an X-ray of a third dose to a breast;
a second X-ray emission unit configured to emit one or more X-rays of a second dose to the breast, the first dose being greater than the second dose;
an X-ray detection unit configured to detect the X-ray of the first dose or the one or more X-rays of the second dose to thereby generate one or more image frames regarding the breast and detect the X-ray of the third dose to generate one or more pilot image frames regarding the breast; and
an image generation unit configured to generate image data regarding the breast based on the generated one or more image frames and generate pilot image data based on the one or more pilot image frames.

2. The apparatus of claim 1, wherein the third dose is less than the first dose.

3. The apparatus of claim 1, further comprising:
a parameter adjustment unit configured to adjust a parameter regarding a dose of an X-ray generated from the first X-ray emission unit or the second X-ray emission unit, based on the pilot image data.

4. The apparatus of claim 3, wherein:
the first X-ray emission unit is further configured to emit the X-ray of the first dose based on the adjusted parameter; and
the second X-ray emission unit is further configured to emit the one or more X-rays of the second dose based on the adjusted parameter.

5. The apparatus of claim 1, wherein the image generation unit is further configured to generate the image data by equalizing the one or more image frames.

6. The apparatus of claim 1, wherein the first X-ray emission unit or the second X-ray emission unit is further configured to emit an X-ray of one or more energy spectrums from a plurality of regions of the breast.

7. The apparatus of claim 6, wherein the X-ray detection unit is further configured to detect the X-ray of the one or more energy spectrums emitted from the plurality of regions of the breast to generate a plurality of image groups comprising the one or more image frames.

8. The apparatus of claim 7, wherein the image generation unit is further configured to compose the one or more image frames constituting the plurality of image groups to generate the image data.

9. The apparatus of claim 8, wherein the image generation unit is further configured to combine and equalize the one or more image frames constituting the plurality of image groups to generate three-dimensional image data regarding the breast.

10. The apparatus of claim 1, wherein : the first X-ray emission unit is fixedly disposed in a center of an X-ray source array, the X-ray source array comprising the first X-ray emission unit and a plurality of second X-ray emission units, the plurality of second X-ray emission units comprising the second X-ray emission unit; and
each of the plurality of second X-ray emission units is fixedly disposed in different positions of the X-ray source array.

11. The apparatus of claim 1, further comprising:
a first X-ray source array, a second X-ray source array and a third X-ray source array, the second and third X-ray source arrays being disposed on opposite sides of the first X-ray source array, wherein:
the first X-ray emission unit is disposed in the first X-ray source array; and
a plurality of second X-ray emission units is disposed in the second X-ray source array or the third X-ray source array, the plurality of second X-ray emission units comprising the second X-ray emission unit.

12. The apparatus of claim 1, wherein:
the first X-ray emission unit is an X-ray source array comprising one or more X-ray sources according to a thermionic emission type; and
the second X-ray emission unit is another X-ray source array comprising one or more X-ray sources according to a field emission type.

13. The apparatus of claim 12, wherein a cathode of the one or more field emission type X-ray sources comprises a carbon nanotube (CNT), a metallic filament tube, or any combination thereof.

14. A method of imaging a breast, comprising:
emitting an X-ray of a first dose to a breast;
emitting an X-ray of a second dose to the breast, the first dose being greater than the second dose;
generating one or more image frames regarding the breast, the generating of the one or more image frames comprising detecting the X-ray of the first dose or the X-ray of the second dose that have passed through the breast;
generating image data regarding the breast based on the generating of the one or more image frames
emitting an X-ray of a third dose to generate pilot image data;
generating one or more pilot image frames regarding the breast, the generating of the one or more pilot image frames comprising detecting the X-ray of the third dose; and
generating the pilot image data based on the generating of the one or more image frames.

15. The method of claim 14, wherein the third dose is less than the first dose.

16. The method of claim 14, further comprising:
adjusting a parameter regarding the X-ray of the first dose or the X-ray of the second dose, based on the pilot image data.

17. The method of claim 16, further comprising:
emitting the X-ray of the first dose based on the adjusted parameter; and
emitting the X-ray of the second dose based on the adjusted parameter.

18. A non-transitory computer readable recording medium storing a program to cause a computer to implement the method of claim 14.

* * * * *